(12) United States Patent
Sinha et al.

(10) Patent No.: US 7,872,121 B2
(45) Date of Patent: Jan. 18, 2011

(54) PROCESS FOR THE REMOVAL OF EXOCYCLIC BASE PROTECTING GROUPS

(75) Inventors: Nanda Dulal Sinha, Milford, MA (US); Satya Kuchimanchi, Milford, MA (US)

(73) Assignee: Avecia Biotechnology, Inc., Milford, MA (US)

( * ) Notice: Subject to any disclaimer, the term of this patent is extended or adjusted under 35 U.S.C. 154(b) by 1126 days.

(21) Appl. No.: 11/578,961

(22) PCT Filed: Apr. 15, 2005

(86) PCT No.: PCT/GB2005/001436
§ 371 (c)(1),
(2), (4) Date: Oct. 19, 2006

(87) PCT Pub. No.: WO2005/100375
PCT Pub. Date: Oct. 27, 2005

(65) Prior Publication Data
US 2009/0221810 A1     Sep. 3, 2009

Related U.S. Application Data

(60) Provisional application No. 60/563,013, filed on Apr. 19, 2004.

(51) Int. Cl.
*C07H 21/00* (2006.01)
(52) U.S. Cl. .................................................. 536/25.31
(58) Field of Classification Search ........................ None
See application file for complete search history.

(56) References Cited

U.S. PATENT DOCUMENTS

| 5,552,539 A | 9/1996 | Duplaa et al. ............. 536/25.31 |
| 5,808,039 A | 9/1998 | Reddy et al. ............... 536/25.3 |
| 6,664,388 B2 * | 12/2003 | Nelson ..................... 536/25.31 |

OTHER PUBLICATIONS (R) Schnetz-Boutaud et al., "Synthesis of Oligonucleotides Containing the Alkali-Labile Pyrimidopurinone Adduct, M1G," Chemical Research in Toxicology, 13(2), 90-95 (2000).*
(S) Fujimoto et al., "Synthesis and Cleavage of Oligonucleotides Containing a 5-Hydroxyuracil Residue in a Defined State," Chemical Research in Toxicology, 10(11), 1254-1258 (1997).*
N. D. Sinha et al, Labile Exocyclic Amine Protection (etc.), Biochimie, 1993, pp. 13-23, vol. 75, Elsevier, Paris.

* cited by examiner

*Primary Examiner*—Lawrence E Crane
(74) *Attorney, Agent, or Firm*—Timothy E. Tinkler

(57) ABSTRACT

Nitrogen-protecting groups are removed from the exocyclic nucleobase portion of a 2'-O protected nucleotide or 2'-halo nucleotide by contacting the nucleotide with an inorganic base. Typical is the removal of t-butylphenoxyacetyl protecting groups from the nucleobase portion of a 2'-O protected nucleotide on which the 2'-O protecting group is t-butyldimethylsilyl, removal or deprotection being accomplished by contact with a potassium carbonate solution.

9 Claims, No Drawings

SEQUENCE LISTING

```
<160> NUMBER OF SEQ ID NOS: 2

<210> SEQ ID NO 1
<211> LENGTH: 23
<212> TYPE: RNA
<213> ORGANISM: Artificial
<220> FEATURE:
<223> OTHER INFORMATION: Oligonulceotide

<400> SEQUENCE: 1
ucgagacacg guguuucggc gcc                                            23

<210> SEQ ID NO 2
<211> LENGTH: 22
<212> TYPE: DNA
<213> ORGANISM: Artificial
<220> FEATURE:
<223> OTHER INFORMATION: Chimeric oligonulceotide
<220> FEATURE:
<221> NAME/KEY: misc_feature
<222> LOCATION: (1)..(3)
<223> OTHER INFORMATION: g represents 2'-O-methyl-substituted RNA
<220> FEATURE:
<221> NAME/KEY: misc_feature
<222> LOCATION: (8)..(8)
<223> OTHER INFORMATION: a represents 2'-O-methyl-substituted RNA
<220> FEATURE:
<221> NAME/KEY: misc_feature
<222> LOCATION: (9)..(9)
<223> OTHER INFORMATION: g represents 2'-O-methyl-substituted RNA
<220> FEATURE:
<221> NAME/KEY: misc_feature
<222> LOCATION: (11)..(11)
<223> OTHER INFORMATION: g represents 2'-O-methyl-substituted RNA
```

```
-continued

<220> FEATURE:
<221> NAME/KEY: misc_feature
<222> LOCATION: (12)..(13)
<223> OTHER INFORMATION: a represents 2'-O-methyl-substituted RNA
<220> FEATURE:
<221> NAME/KEY: misc_feature
<222> LOCATION: (15)..(15)
<223> OTHER INFORMATION: g represents 2'-O-methyl-substituted RNA
<220> FEATURE:
<221> NAME/KEY: misc_feature
<222> LOCATION: (18)..(18)
<223> OTHER INFORMATION: a represents 2'-O-methyl-substituted RNA
<220> FEATURE:
<221> NAME/KEY: misc_feature
<222> LOCATION: (21)..(21)
<223> OTHER INFORMATION: g represents 2'-O-methyl-substituted RNA

<400> SEQUENCE: 2
gggaauuagu gaauguuauu gt                                              22
```

PROCESS FOR THE REMOVAL OF EXOCYCLIC BASE PROTECTING GROUPS

RELATED APPLICATIONS

This application is the U.S. National Stage of International Application No. PCT/GB2005/001436, filed on Apr. 15, 2005, published in English, which claims the benefit of U.S. Provisional Application No. 60/563,013, filed on Apr. 19, 2004. The entire teachings of the above applications are incorporated herein by reference.

The present invention concerns a process for the removal of exocyclic base protecting groups from oligoribonucleotides.

The pharmaceutical potential of oligonucleotide medicines has lead to increasing demand for more effective methods of preparation of such compounds. Whilst much attention has hitherto been focussed on deoxyribonucleotides, the recent interest in the therapeutic and research uses of so-called small interfering ribonucleic acids has resulted in an increased need for improved oligoribonucleotide synthesis methodologies.

The synthesis of oligonucleotides is a complex, multi-step procedure, usually involving the assembly of a desired oligonucleotide by sequential coupling of chosen nucleosides onto a nascent oligonucleotide. In order to obtain the correct product, it is important that the coupling occurs between the correct reactive sites. However, nucleosides and nascent oligonucleotides comprise a number of different potential reactive sites which could potentially interfere with the coupling unless they were prevented from reacting. This has led to the evolution of a number of protection strategies for the various different potentially interfering sites. However, once the assembly has been completed, the various protecting groups must be removed in a deprotection step but without significant degradation of the end-product.

Whilst ribonucleotides are superficially similar to deoxyribonucleotides, the presence of an extra potentially reactive site at the 2'-position makes them particularly sensitive to degradation during the post-assembly treatment process. Accordingly, methods which can be applied routinely in the field of deoxyribonucleotides cannot necessarily be simply transferred to the field of ribonucleotides. In particular, ribonucleotides are known to be particularly sensitive to contact with aqueous bases, whereas deoxyribonucleotides are not.

One class of protecting groups routinely employed in oligonucleotide synthesis are exocyclic base protecting groups, which protect otherwise reactive exocyclic amino and lactam groups present in nucleobases. Many of these exocyclic base protecting groups are carbonyl compounds, which form an amide moiety. Commonly, such groups are removed by treatment with an anhydrous alkyl amine, especially methylamine. However, methylamine is difficult to handle on a large scale, and accordingly, it would be desirable to identify alternative processes for the removal of exocyclic base protecting groups from ribonucleotides.

According to the present invention, there is provided a process for removal of exocyclic nucleobase nitrogen-protecting groups from a protected oligonucleotide which comprises contacting the protected oligonucleotide with a solution of an inorganic base, characterised in that the protected oligonucleotide comprises at least one 2'-O-protected nucleotide or 2'-halo-, such as a 2'-fluoro-, nucleotide, and that the inorganic base is selected from the group consisting of lithium hydroxide, lithium carbonate, sodium carbonate and potassium carbonate.

Oligonucleotides which can be deprotected by the process of the present invention comprise at least one 2'-O-protected nucleotide or at least one 2'-halo nucleotide. 2'-O protecting groups which may be present include alkyl or substituted alkyl blocking groups, such as methyl and methoxyethyl groups; acetate-protecting groups, such as acetylorthoacetate; piperidinyl-type protecting groups, such as 1-(2-fluorophenyl)-4-methoxypiperidine-4-yl (Fpmp) and 1-(2-chlorophenyl)-4-methoxypiperidine-4-yl (Cpmp); and particularly silyl protecting groups, such as a tri($C_{1-4}$alkyl) silyl-protecting groups. The oligonucleotides may comprise only 2'-O-protected nucleotides, only 2'-halo-nucleotides or a mixture of both 2'-O-protected nucleotides and 2'-halo-nucleotides. In many embodiments, the oligonucleotides comprise a mixture of deoxyribonucleotides and 2'-O-protected nucleotides, a mixture of deoxyribonucleotides and 2'-halo nucleotides or a mixture of deoxyribonucleotides, 2'-O-protected nucleotides and 2'-halo nucleotides. One or more other nucleotides, such as 2'-C-allyl nucleotides, 2'-amino- or 2'-protected amino nucleotides, abasic nucleotides and inverted nucleotides, may also be present. Whilst the invention is described primarily with reference to D-nucleotides, it will be recognised that the invention is equally applicable to L-nucleotides, and to mixtures of L and D nucleotides.

Oligonucleotides which can be deprotected by the process of the present invention may be prepared by solution phase chemistry or, most commonly, by solid phase chemistry, in which the oligonucleotide is attached to a solid support, usually via a cleavable linker. In many embodiments, attachment to a solid support is via the 3'-position. The deprotection may take place in the solution phase, but is preferably achieved whilst the oligonucleotide is attached to a solid support.

Protected oligonucleotides which can be subjected to the process of the present invention are commonly compounds wherein the 5'-position is either unprotected or protected by an acid labile protecting group for example a trityl; substituted trityl, such as dimethoxytrityl; or a pixyl group; and the 3'-position is unprotected; protected with an acyl protecting group, such as an acetyl or levulinoyl group, or a silyl protecting group, or, preferably, attached to a solid support, most preferably via a cleavable linker.

For 2'-O-protected nucleotides, the 2'-position may be protected with a removable protecting group, such as a silyl protecting group, for example a trialkyl, especially a tri($C_{1-4}$-alkyl) silyl protecting group, preferably a t-butyldimethylsilyl protecting group or the 2'-position may be protected by a less easily removed group, for example an alkyl group, such as a methyl group, or a substituted alkyl group, such as a methoxyethyl group.

Preferred oligonucleotides which can be deprotected are compounds of the formula:

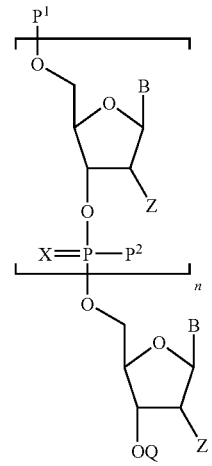

wherein $P^1$ is an acid labile protecting group, preferably a trityl, monomethoxytrityl or dimethoxytrityl group. Each B independently is a nucleobase, provided that at least one nucleobase comprises a base labile protecting group. Each $P^2$ independently is a phosphorus protecting group, commonly a cleavable phosphorus protecting group employed in oligonucleotide synthesis, and preferably a group of formula —$OR^1$ or —$SR^1$ wherein each $R^1$ independently represents an alkyl, alkenyl, aryl or aralkyl group. Preferred groups of formula —$OR^1$ or —$SR^1$ include groups of formula —$OCH_2CH_2CN$, —$SCH_2CH_2CN$, —$O$—$CH_2CH_2Si(CH_3)_2$ $C_6H_5$, —$O$—$CH_2CH_2$—$S(O)_2$—$CH_2CH_3$, —$O$—$CH_2CH_2C_6H_4$—$NO_2$, —$S$—$CH_2CH_2$—$Si(CH_3)_2$ $C_6H_5$, —$S$—$CH_2CH_2$—$S(O)_2$—$CH_2CH_3$, or —$S$—$CH_2CH_2C_6H_4$—$NO_2$. Each Z independently represents H, F or $OP^3$ wherein each $P^3$ independently represent an alkyl, preferably a methyl group, an alkoxyalkyl, preferably a methoxyethyl group, or a silyl protecting group, preferably a tri($C_{1-4}$alkyl) group, provided that at least one Z represents F or $OP^3$. It is especially preferred that at least one $P^3$ represents a tri($C_{1-4}$alkyl)silyl group, most preferably a t-butyldimethylsilyl group. The process of the present invention has been found to be particularly suited to compounds having one or more of:

a) 100% of Z representing O-silyl protecting groups;

b) from 40 to 60% of Z representing F; and c) from 40 to 60% of Z representing O-methyl.

In certain embodiments, up to 10% of Z represents O-silyl; from 45 to 55% of Z represents F, with the remainder representing H or O-methyl. Each X is independently O or S. n is a positive integer, preferably from 1 to about 50, most preferably from 15 to 30, and Q represents a protecting group, a solid support or a cleavable linker attached to a solid support.

Nucleobases which may be present in oligonucleotides which can be deprotected by the process of the present invention include natural and/or unnatural nucleobases, including adenine, guanine, cytosine, thymine, uracil, 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

Protecting groups which can be removed by the process of the present invention are base-labile protecting groups for exocyclic nitrogens, such as exocyclic amino and lactam groups, and are well know to those skilled in the art. Protecting groups which are employed on exocyclic amino or lactam groups include in particular include those protecting groups which form base-labile amides or imides with the group to be protected. Examples include substituted and un-substituted benzoyl, acetyl, isobutyryl and phenoxyacetyl groups. Preferred protecting groups are benzoyl, acetyl, isobutyryl, phenoxyacetyl and t-butylphenoxyacetyl protecting groups. Particular examples of the process of the present invention include the removal of benzoyl protecting groups from the N-6 of adenosine, the removal of benzoyl or acetyl protecting groups from the N-4 of cytosine and the removal of isobutyryl from the N-2 of guanosine. Uracil and thymidine generally do not require protection, although may occasionally be employed in protected form. Particular examples of the process of the present invention applied to protected uracil or thymidine include the removal of phenoxyacetyl or t-butylphenoxyacetyl protecting groups from the N-3 position.

Preferred inorganic bases which can be employed in the process of the present invention are sodium and potassium carbonate, the most preferred base being potassium carbonate.

The process of the present invention may employ either a solely aqueous solution of the inorganic base, or a solely organic solution. However, in many embodiments, it is preferred to employ a mixture of water and a water-miscible organic solvent. Examples of suitable organic solvents include water miscible ethers, such as tetrahydrofuran; amides, such as N-methylpyrrolidinone and dimethylformamide; sulphoxides, such as dimethylsulfoxide; nitriles, such as acetonitrile; and alcohols, such as methanol and ethanol. In many embodiments, the solvent comprises up to 30% water by volume, such as from 1-20% water by volume, especially about 2-10% water by volume. An especially preferred solvent is a 5% by volume mixture of water in methanol.

The process according to the present invention is preferably carried out at a temperature in the range of from 0° C. to 50°, and preferably at ambient temperature, such as from about 15 to 25° C. The process is carried out until substantially all of the exocyclic amine and lactam protecting groups have been removed. It will be recognised that the time required will vary depending on a number of factors, including, for example, the precise nature of the protecting groups, the temperature employed, and the concentration of the inorganic base. In many embodiments, contact with the solution of the inorganic base takes place over up to 24 hours, such as from 2-24 hours. In certain embodiments, a temperature of about 60° C. for about 3 hours is employed.

The process of the present invention is commonly applied to oligonucleotides after the removal of phosphorus protecting groups, such as betacyanoethyl groups. Where a removable 2'-O protecting group is employed, the process of the present invention precedes removal of the 2'-O protecting group. When the oligonucleotide has been prepared by solid phase synthesis, the process of the present invention preferably also serves to cleave the oligonucleotide from the solid support.

2'-O-protecting groups can be removed by the use of methods known in the art for removal of the chosen protecting group. For example, a 2'-O-(trialkyl)silyl protecting group may be removed by treatment with t-butylammonium fluoride or triethylamine.3HF.

After deprotection and cleavage, the oligonucleotides are preferably purified using one or more standard techniques known in the art, such as, ion-exchange chromatography, reverse phase chromatography, precipitation from an appropriate solvent and ultra-filtration.

The present invention is illustrated, without limitation, by the following examples.

EXAMPLE 1

An oligonucleotide having the sequence (5'-rUrCrG-rArGrA-rCrArC-rGrGrU-rGrUrU-rUrCrG-rGrCrG-rCrC-3') [Sequence No. 1] attached to a CPG support was prepared using phosphoramidite chemistry using an Amersham Biosciences OligoPilot™ II synthesiser. Conventional 5'-dimethoxytrityl betacyanoethyloxy diisopropyl amidites were employed. rU nucleotides were protected at the 2'-position by t-butyldimethylsilyl groups; rC nucleotides were protected at the 2'-position by t-butyldimethylsilyl groups and at N-4 by acetyl groups; rG nucleotides were protected at the 2'-position by t-butyldimethylsilyl groups and at N-2 by isobutyryl groups; rA nucleotides were protected at the 2'-position by t-butyldimethylsilyl groups and at N-6 by benzoyl groups. Coupling was achieved by using 2 equivalents of amidite to supported nucleotide (0.2M in acetonitrile), with 4 equivalents of N-methylimidazole saccharinate (0.2M in acetonitrile) for a contact time of 10 minutes (with recycling). Oxidation was achieved with 50 mM Iodine in pyridine containing 4% water (v/v) for 6 minutes. Capping employed a solution of 20% v/v isobutyric anhydride and 30% v/v pyridine in acetonitrile for 7 minutes in flow-through mode. Detritylation employed 3% v/v dichloroacetic acid in toluene for 1 minute.

Betacyanoethyl groups were removed by treatment with 2 column volumes of 50% v/v t-butylamine solution in acetonitrile for 60 minutes. The column was then washed with acetonitrile to remove residual t-butylamine, and then dried by filtration.

50 mg of the dried support containing the oligonucleotide were taken, and treated by the following method in order to remove exocyclic base protecting groups, and cleave the oligonucleotide from the solid support:

250 μl of $K_2CO_3$ solution (0.1M in methanol containing 20% v/v water) and 250 μl of N-methylimidazole solution (5M in methanol) was added to the support and incubated at 62° C. for 18 hours. The solid support was separated from the residual solution, and washed with 250 μl of dimethylsulfoxide. The residual solution, combined with the dimethylsulfoxide washings was treated with 450 μl of triethylamine.3HF for 4 hours at 62° C. The solution obtained was then added to 4 ml cold (−78° C.) aqueous $NH_4CO_3$ solution (1.5M) to adjust the pH to ca. 7.

The oligonucleotide was analysed by desalting using a Nap column from Amersham Biosciences, followed by IEX-HPLC and MALDI-TOF analysis. The results showed complete removal of exocyclic protecting groups. No degradation of the product oligonucleotide was observed.

EXAMPLE 2

A 22-mer chimeric oligonucleotide having the sequence 5'-ggg-rArAfU-fUag-fUga-afUg-fUfUa-fUfUg-3'-3'-dT-5' (wherein "a" and "g" represent 2'-O-methyl-substituted RNA, and the prefix "f" denotes a 2'-Fluoro-substituted deoxyribo moiety) was prepared by the same general method as for example 1, using corresponding phosphoramidites.

100 mg of the dried support containing the oligonucleotide were taken, and treated by the following method in order to remove exocyclic base protecting groups, and cleave the oligonucleotide from the solid support:

1 ml of $K_2CO_3$ solution (0.1M in methanol containing 5% v/v water) was added to the support and incubated at 62° C. for 3 hours. The solid support was separated from the residual solution, and washed with 1 ml of dimethylsulfoxide. The residual solution, combined with the dimethylsulfoxide washings was treated with 1 ml of triethylamine.3HF for 2 hours at room temperature, and two further hours at 62° C. The solution obtained was then added to 4 ml cold (−78° C.) aqueous $NH_4CO_3$ solution (1.5M) to adjust the pH to ca. 7.

The oligonucleotide was analysed by desalting using a Nap column from Amersham Biosciences, followed by IEX-HPLC and MALDI-TOF analysis. The results showed complete removal of exocyclic protecting groups. No degradation of the product oligonucleotide was observed.

The invention claimed is:

1. A process for removal of exocyclic nucleobase base labile nitrogen-protecting groups selected from the group consisting of benzoyl, acetyl, isobutyryl, phenoxyacetyl and t-butylphenoxyacetyl groups, from a protected oligoribonucleotide which comprises contacting the protected oligoribonucleotide with a solution of an inorganic base, wherein the protected oligoribonucleotide further comprises at least one 2'-O-protected nucleotide or 2'-halonucleotide, and the inorganic base is selected from the group consisting of lithium hydroxide, lithium carbonate, sodium carbonate and potassium carbonate.

2. A process according to claim 1, wherein the 2'O-protected oligoribonucleotide comprises at least one 2'-O-tri($C_{1-4}$alkyl)silyl-protected nucleotide.

3. A process according to claim 1, wherein the inorganic base is potassium carbonate.

4. A process according to claim 1, wherein the inorganic base is employed as a solution in a mixture of water and methanol or ethanol, said mixture comprising up to 30% water by volume.

5. A process according to claim 1, wherein the inorganic base is potassium carbonate.

6. A process according to claim 1, wherein the inorganic base is potassium carbonate, employed as a solution in a mixture of water and methanol or ethanol, said mixture comprising up to 30% water by volume.

7. A process for the preparation of a deprotected oligoribonucleotide which comprises the steps of:
   a) providing a protected oligoribonucleotide that comprises at least one 2'-O-tri($C_{1-4}$alkyl)silyl-protected nucleotide;
   b) removing exocyclic nucleobase base labile nitrogen-protecting groups selected from the group consisting benzoyl, acetyl, isobutyryl, phenoxyacetyl and t-butylphenoxyacetyl groups from the protected oligoribonucleotide by contact with a solution of an inorganic base selected from the group consisting of lithium hydroxide, lithium carbonate, sodium carbonate and potassium carbonate; and
   c) removing 2'-O-tri($C_{1-4}$-alkyl)silyl groups by contact with a solution of t-butylammonium fluoride or triethylamine.3HF.

8. A process according to claim 7, wherein the inorganic base is potassium carbonate.

9. A process according to either claim 7 or 8, wherein the inorganic base is employed as a solution in a mixture of water and methanol or ethanol, said mixture comprising up to 30% water by volume.

* * * * *